United States Patent
Heffron

(10) Patent No.: US 10,037,646 B2
(45) Date of Patent: Jul. 31, 2018

(54) MANAGING MEDICATIONS AT THE BEDSIDE

(75) Inventor: David Heffron, San Diego, CA (US)

(73) Assignee: CareFusion 303, Inc., San Diego, CA (US)

(*) Notice: Subject to any disclaimer, the term of this patent is extended or adjusted under 35 U.S.C. 154(b) by 0 days.

(21) Appl. No.: 11/928,928

(22) Filed: Oct. 30, 2007

(65) Prior Publication Data

US 2009/0108011 A1    Apr. 30, 2009

(51) Int. Cl.
| | |
|---|---|
| B65G 59/00 | (2006.01) |
| B65H 9/00 | (2006.01) |
| G06Q 50/00 | (2012.01) |
| G07F 11/00 | (2006.01) |
| G06Q 50/24 | (2012.01) |
| G07F 9/02 | (2006.01) |
| G07F 17/00 | (2006.01) |
| G06F 19/00 | (2018.01) |
| A61G 12/00 | (2006.01) |
| A61J 7/00 | (2006.01) |

(52) U.S. Cl.
CPC .......... *G07F 11/00* (2013.01); *G06F 19/3462* (2013.01); *G06Q 50/24* (2013.01); *G07F 9/026* (2013.01); *G07F 17/0092* (2013.01); *A61G 12/001* (2013.01); *A61J 7/0084* (2013.01)
USPC .......................... 700/237; 700/240; 700/232

(58) Field of Classification Search
USPC ................................................. 700/231–244
See application file for complete search history.

(56) References Cited

U.S. PATENT DOCUMENTS

| | | | |
|---|---|---|---|
| 4,785,969 A | | 11/1988 | McLaughlin |
| 5,036,462 A | * | 7/1991 | Kaufman .............. A61J 7/0084 221/12 |
| 5,842,976 A | * | 12/1998 | Williamson .................. 600/300 |
| 6,175,779 B1 | * | 1/2001 | Barrett .......................... 700/242 |
| 6,775,591 B1 | | 8/2004 | Shoenfeld |
| 6,935,560 B2 | * | 8/2005 | Andreasson et al. ......... 235/385 |
| 7,140,542 B2 | * | 11/2006 | Andreasson et al. ......... 235/385 |

(Continued)

FOREIGN PATENT DOCUMENTS

| | | |
|---|---|---|
| EP | 1075831 A1 | 2/2001 |
| JP | 63-212361 | 1/1988 |

(Continued)

OTHER PUBLICATIONS

International Search Report from PCT/US2008/081802, dated Aug. 26, 2009.

(Continued)

*Primary Examiner* — Michael Collins
(74) *Attorney, Agent, or Firm* — McDermott Will & Emery LLP

(57) ABSTRACT

Systems and methods for dispensing medications to hospitalized individuals through a first apparatus containing optional medications that is configured to be replenished by optional medication from a central storage location. Some embodiments provide that the first apparatus is associated with an individual patient. The first apparatus is preferably secured at a location near the individual patient, such as, for example, within the individual patient's room. By creating multiple dispensing apparatuses, a caregiver who administers required medications no longer has to retrieve optional medications from a central storage location.

19 Claims, 4 Drawing Sheets

(56) References Cited

U.S. PATENT DOCUMENTS

| | | | |
|---|---|---|---|
| 7,155,306 B2* | 12/2006 | Haitin et al. | 700/242 |
| 7,175,081 B2* | 2/2007 | Andreasson et al. | 235/385 |
| 7,182,256 B2* | 2/2007 | Andreasson et al. | 235/385 |
| 7,232,066 B2* | 6/2007 | Andreasson et al. | 235/385 |
| 7,258,249 B1* | 8/2007 | Frederick et al. | 221/282 |
| 7,668,620 B2* | 2/2010 | Shoenfeld | G06F 19/3462 700/231 |
| 7,668,630 B2 | 2/2010 | Weber et al. | |
| 7,689,318 B2 | 3/2010 | Draper | |
| 7,693,603 B2 | 4/2010 | Higham | |
| 7,734,372 B2* | 6/2010 | Shoenfeld | G06F 19/3462 700/231 |
| 7,885,725 B2* | 2/2011 | Dunn | G06F 19/3462 700/236 |
| 8,111,159 B2* | 2/2012 | Andreasson et al. | 340/572.1 |
| 8,326,455 B2* | 12/2012 | Dunn | G06F 19/3462 221/211 |
| 8,473,097 B2 | 6/2013 | Shoenfeld | |
| 8,700,211 B2 | 4/2014 | Shoenfeld | |
| 8,891,243 B2 | 11/2014 | Tanaka et al. | |
| 2003/0120384 A1* | 6/2003 | Haitin | A61G 12/001 700/242 |
| 2003/0191670 A1* | 10/2003 | Hatcher | G06F 19/324 705/2 |
| 2004/0010425 A1* | 1/2004 | Wilkes et al. | 705/3 |
| 2005/0062238 A1* | 3/2005 | Broadfield | A61G 12/001 280/1 |
| 2006/0032918 A1* | 2/2006 | Andreasson et al. | 235/385 |
| 2006/0065726 A1* | 3/2006 | Andreasson et al. | 235/385 |
| 2006/0136095 A1 | 6/2006 | Rob et al. | |
| 2006/0229551 A1 | 10/2006 | Martinez et al. | |
| 2006/0265102 A1 | 11/2006 | Bain | |
| 2007/0023513 A1* | 2/2007 | Andreasson et al. | 235/385 |
| 2007/0043469 A1 | 2/2007 | Draper | |
| 2007/0088461 A1* | 4/2007 | Haitin | A61G 12/001 700/241 |
| 2007/0093932 A1* | 4/2007 | Abdulhay | A61J 7/0084 700/231 |
| 2007/0156282 A1* | 7/2007 | Dunn | G06F 19/3462 700/244 |
| 2007/0227204 A1* | 10/2007 | Shoenfeld | A61B 50/10 70/101 |
| 2007/0244598 A1* | 10/2007 | Shoenfeld | 700/236 |
| 2009/0108011 A1 | 4/2009 | Heffron | |
| 2011/0125317 A1* | 5/2011 | Dunn | G06F 19/3462 700/236 |
| 2013/0079924 A1 | 3/2013 | Garda et al. | |
| 2014/0163726 A1 | 6/2014 | Shoenfeld et al. | |
| 2014/0297027 A1 | 10/2014 | Tylenda et al. | |

FOREIGN PATENT DOCUMENTS

| | | |
|---|---|---|
| JP | 2004-210486 | 7/2004 |
| JP | 2004-528141 | 9/2004 |
| JP | 2006-305099 | 11/2006 |
| RU | 2004133669 A | 7/2005 |
| WO | WO2002-099231 | 12/2002 |
| WO | WO-2012142314 A1 | 10/2012 |
| WO | WO-2013173015 A1 | 11/2013 |

OTHER PUBLICATIONS

International Preliminary Report on Patentability from related PCT App. No. PCT/US2008/081802, dated May 4, 2010.
Japanese Office Action dated Dec. 18, 2012.
Australian Examination Report No. 3 in Australian Application No. 2008318610, dated Jul. 8, 2013, 3 pages.
Australian Examination Report No. 1 in Australian Application No. 2008318610, dated Jul. 19, 2012, 3 pages.
Australian Examination Report No. 2 in Australian Application No. 2008318610, dated Mar. 13, 2013, 3 pages.
Australian Notice of Acceptance in Australian Application No. 2008318610, dated Oct. 11, 2013, 1 page.
Canadian Office Action in Canadian Application No. 2703508, dated Jul. 15, 2013, 2 pages.
Canadian Office Action in Canadian Application No. 2703508, dated Sep. 30, 2014, 3 pages.
First Office Action in Chinese Application No. 200880113906.7, dated Mar. 7, 2012, 11 pages.
New Zealand Office Action in New Zealand Application No. 584756, dated Jul. 12, 2011, 2 pages.
Notification of the Decision of Rejection in Chinese Application No. 200880113906.7, dated Oct. 15, 2011, 17 pages.
Russian Office Action in Russian Application No. 2010121904, dated Nov. 23, 2012, 14 pages.
Russian Decision of Grant in Russian Application No. 2010121904, dated Dec. 6, 2013, 7 pages.
Russian Office Action in Russian Application No. 2010121904, dated Jul. 15, 2013, 11 pages.
Chinese Second Office Action in Chinese Application No. 200880113906.7, dated Apr. 29, 2015, 22 pages.
Canadian Office Action for Application No. 2703508, dated Aug. 20, 2015, 4 pages.
Chinese Third Office Action for Application No. 200880113906.7, dated Nov. 4, 2015, 20 pages.
Canadian Office Action for Application No. 2703508, dated Jul. 19, 2016, 5 pages.
Chinese Fifth Office Action for Application No. 200880113906.7, dated Aug. 9, 2016, 10 pages excluding English translation.
Chinese Office Action for Application No. 200880113906.7, dated Feb. 7, 2017, 11 pages excluding translation.
Canadian Office Action for Application No. 2703508, dated Jun. 13, 2017, 4 pages.
Chinese Fourth Office Action for Application No. 200880113906.7, dated Mar. 18, 2016, 11 pages excluding translation.
European Office Action for Application No. 08843739.7, dated Mar. 23, 2016, 6 pages.
International Search Report and Written Opinion for Application No. PCT/US2015/064105, dated Feb. 9, 2016, 11 pages.

* cited by examiner

MANAGING MEDICATIONS AT THE BEDSIDE

STATEMENT AS TO RIGHTS TO INVENTIONS MADE UNDER FEDERALLY SPONSORED RESEARCH OR DEVELOPMENT

Not Applicable.

CROSS-REFERENCES TO RELATED APPLICATIONS

Not Applicable.

BACKGROUND

Everyday, patients hospitalized because of age, infirmities, or accidents, receive unsatisfactory care. Dissatisfaction can arise when a request for medication is responded to in an untimely manner. In some instances, hours can pass without response to a patient's requests. Often, the untimely response results from the overburdening of caregivers that occurs due to the numerous tasks associated with the daily care of hospitalized individuals, including dispensing and administrating medications.

Caregivers use a centralized inventory system for dispensing and administering medications. In this system, medications are stored in a centralized area. Both required and optional medications are dispensed and administered to each patient by retrieving medications from a centralized inventory onto a movable cart. In some instances, a caregiver follows a prescribed schedule for administering required medication to a patient and provides optional medication upon request by the patient. Optional medication often includes pro re nata (PRN) medication. PRN medication refers to dosages of prescribed medication that are not scheduled, and administration is left to the caregiver or the patient's prerogative. PRN is often added to the prescribed directions for medication used to treat symptoms (e.g., pain/fever, constipation, insomnia, anxiety, nausea/vomiting). Most often PRN medications are analgesics, such as paracetamol (Tylenol) or hydrocodone (Vicodin), laxatives, such as coloxyl, sleeping aids (sedatives), such as zolpidem (Ambien) or lorazepam (Ativan), and antiemetics, such as ondansetron or dimenhydrinate (Gravol). These medications can include over-the-counter drugs that would be readily available to the patient but for the patient's admittance into the hospital or care facility.

Upon request by the patient to receive the optional medication, the caregiver retrieves the medication from the centralized inventory and returns to the patient to administer the optional medication. The patient often requests the optional medication during administration of the required medication, at which time, caregivers proceed to each patient's room dispensing and administering the required medications. When optional medication, such as PRN medication, is requested, the caregiver exits the patient's room and retrieves the optional medication from the centralized inventory and returns to the patient's room to administer the medication. After administration of the optional medication, the caregiver proceeds to the next patient to administer the required medication, and this patient may also request optional medication. Accordingly, the caregiver again returns to the centralized inventory to retrieve the requested optional medication and returns to the patient for administration.

SUMMARY

The present disclosure provides methods and systems for dispensing medication. The methods and systems dispense optional medications from a fixed dispensing apparatus located in, or in close proximity to, an individual patient's room, while required medications are dispensed from a movable dispensing apparatus. By providing multiple dispensing apparatuses, increased satisfaction of a hospitalized patient is realized by a decrease in delay time for receiving requested medications. These methods and systems reduce the number of times that a caregiver is required to return to a central storage location to retrieve optional medication for a patient. Moreover, these methods and systems provide an efficient manner for a caregiver to administer medications to a patient while maintaining control over the medications by the care facility.

In some embodiments, a system for dispensing medication from within a patient's room is described. The system preferably includes a first dispenser positioned within, or in close proximity to, the patient's room that is configured to contain optional medication and to provide access to the optional medication only by authorized personnel and a central storage location that stores optional medication for replenishing the first dispenser for optional medication.

In some embodiments, the first dispenser is affixed within the patient's room and the optional medication comprises PRN medication. In further embodiments, the first dispenser monitors what medications are stored within and dispensed from the first dispenser. In some embodiments, the first dispenser is configured to associate medication dispensed from the first dispenser with the patient for billing purposes, is configured to dispense optional medication by instructions provided from the central storage location, and/or is configured to provide access to only one dose of an optional medication upon a request for access to the optional medication. In further embodiments, a mobile dispenser is configured to contain required medication for administration to the patient and the central storage location stores required medication for replenishing the mobile dispenser.

In some embodiments, a method for dispensing medication in a care facility is described. The method preferably includes dispensing a first medication from a dispenser if a request is obtained by a patient for an optional medication, the dispenser being associated with and affixed to a location within a room of the care facility in which the patient is staying, and replenishing the dispenser with the first medication from medication stored at a central storage location.

In some embodiments, the method further includes administering the first medication to the patient by care facility personnel. Some embodiments provide that dispensing the first medication from the dispenser includes unlocking a security mechanism on the first apparatus. In further embodiments, dispensing the first medication includes providing access to one dose of the first medication and/or dispensing PRN medication. Some methods described herein further include logging administrative information corresponding to accessing medication within the dispenser, automatically tracking by the dispenser which medications have been dispensed from the dispenser, and/or automatically billing a patient for optional medication dispensed from the dispenser. In some embodiments, dispensing the first medication includes remotely providing instructions to the dispenser to allow the patient to have access to the optional medication. Some methods provide that replenishing the first medication includes storing optional medication within the dispenser based on projected needs of the patient.

Some embodiments provide that the dispenser is accessed by at least one of a lock and key set, fingerprint recognition device, and voice recognition device.

In yet further methods described herein for dispensing different types of medication to a plurality of patients, the methods include selectively dispensing an optional medication from an affixed secured apparatus located within an individual patient's room in response to a request for the optional medication and dispensing a required medication for the individual patient from a portable apparatus.

In some embodiments, the methods further include repeating the dispensing method for each individual patient within the plurality of patients. The methods can further provide that dispensing the optional medication from the affixed apparatus includes unlocking a security mechanism on the secured apparatus. In some embodiments, the methods further include automatically logging administrative information corresponding to dispensing from the affixed secured apparatus and managing the administrative information from a centralized storage location.

In accordance with certain aspects of the present disclosure, a method for dispensing medications is presented. The method includes dispensing a first medication from a first apparatus if a request is obtained for medication that corresponds to an optional medication. The first apparatus is associated with an individual patient. The method also includes dispensing a second medication from a second apparatus corresponding to a required medication. The second apparatus is associated with a plurality of patients.

According to other aspects of the present disclosure, a method for dispensing medications to each individual within a plurality of patients is presented. The method includes dispensing an optional medication from a fixed apparatus located within an individual patient's room if a request for the optional medication is obtained. In addition, the method includes dispensing a required medication from a movable apparatus associated with the plurality of patients.

According to yet other aspects of the present disclosure, a system for dispensing medications to a plurality of patients is presented. The system includes a first apparatus for dispensing a first medication corresponding to an optional medication. The first apparatus is associated with an individual patient. The system also includes a second apparatus for dispensing a second medication corresponding to a required medication. The second apparatus is associated with the plurality of patients.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure. In the drawings.

DETAILED DESCRIPTION

The present disclosure generally relates to medications. More specifically, the present disclosure relates to dispensing medications from separately placed apparatuses to increase the efficiency of caregivers and the overall satisfaction of patients. In accordance with the present disclosure, an individualized dispensing apparatus located near each individual patient carries optional medications. A separate dispensing apparatus carries required medications and is capable of servicing multiple patients. By using more than one apparatus to dispense medications, caregivers do not have to retrieve optional medications at a central storage location each time a request has been made for the optional medications. Neither does the caregiver have to return to stock unused medications.

Two types of medications are given to patients: required and optional. Medications which treat the condition of the patient are called required medications and are patient specific. Often, these medications are associated with a prescription that is issued by a medical professional. Required medications are generally more expensive than optional medications.

Optional medications are generally used to relieve pain and discomfort. These can include PRN medications. PRN medications, as used herein, is intended to have its plain and ordinary meaning, which includes, without limitation, medications that are made available for a patient if needed, but which are not part of a daily prescribed regimen. There is generally no requirement on the times and doses used for optional medications, but the amount used may be limited by the specific manufacturer of the optional medication. Optional medications are characterized as being relatively inexpensive.

Figure 1A:
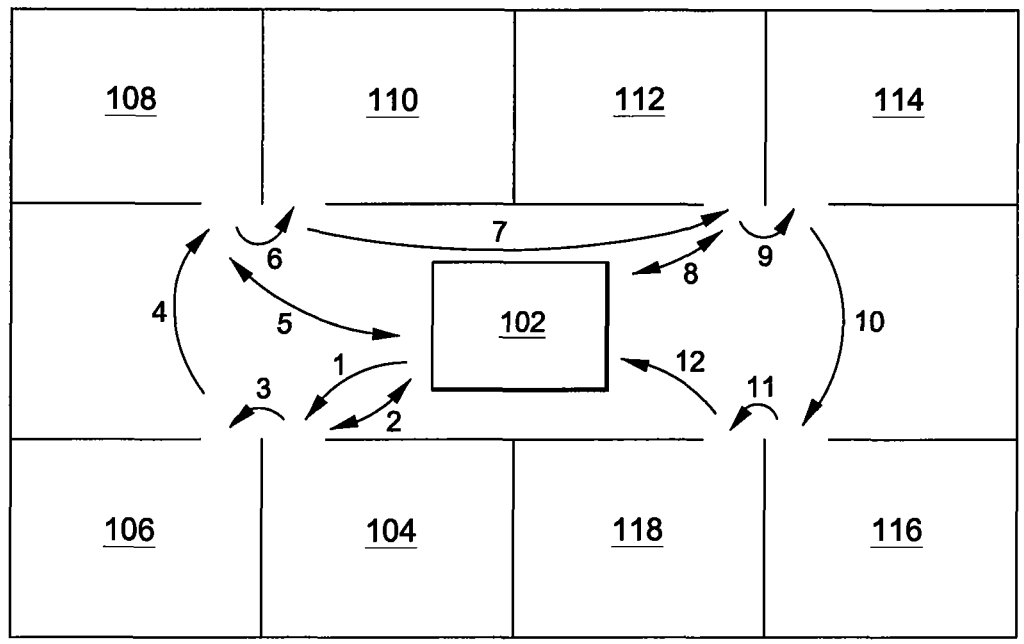
FIG. 1a is a diagram of a hospital that indicates a path taken by a caregiver to dispense medications to patients.
Figure 1B:
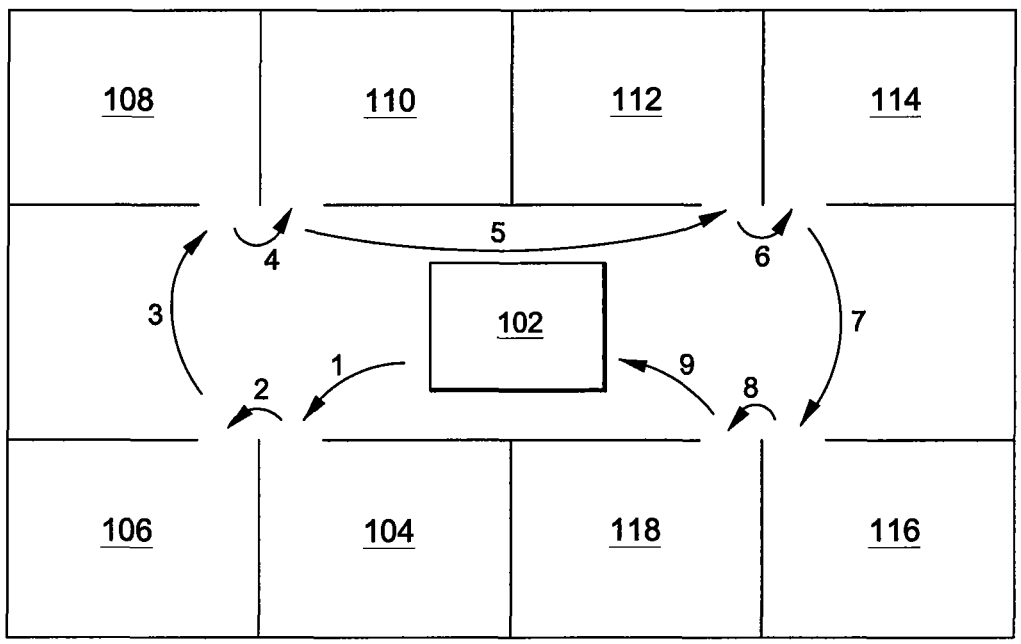
FIG. 1b is a diagram of a hospital that indicates another path taken by a caregiver to dispense medications to patients.

Now referring to FIGS. 1a and 1b, diagrams 100 indicating paths taken by caregivers to dispense medications to patients are presented. In the middle of the diagrams 100, a central storage location 102 is shown. Required and optional medications are kept at the central storage location 102. Preparation of required medications are made at the central storage location 102 to distribute them to the individual patients by the caregivers. The medications are placed on trays for each patient and placed onto a movable medical cart or medical station. As used herein, the term cart is a broad term, is used in its ordinary sense, and is intended to include, without limitation, a decentralize storage system or apparatus, which can be, for example, a MEDSTATION® provided by Cardinal Health. By utilizing the movable cart, caregivers can administer the individualized required medications for each hospitalized patient without returning to the central storage location 102 for each patient's required medication needs.

To maintain the appropriate amount of required and optional medications, the central storage location 102 tracks information regarding the amount of medications left and whether more medications need to be ordered. In certain embodiments, the information tracked by the central storage location 102 is received directly from the caregivers. Alternatively, the information is received from dispensing apparatuses. Each dispensing apparatus sends administrative information to an electronic inventory management device used at the central storage location 102. The electronic inventory management device then processes the administrative information.

Continuing with FIGS. 1a and 1b, a plurality of patients' rooms 104-118 are shown. Each patient's room is spaced apart from one another. One skilled in the art would understand that a room can include physical barriers such as walls and doors. Alternatively, the rooms can be partitioned by screening devices such as cloth dividers. Although eight rooms 104-118 are shown, the hospital can include more or less rooms dependent on the size and constraints of the hospital.

With reference now to FIG. 1a, a caregiver's route using a single dispensing apparatus for each individual's required medicinal needs is presented. The route begins when the caregiver proceeds to room 104 to administer required medications to the patient therein. During the administering of the required medication, the patient requests an optional medication for his/her headache or similar type of infirmity. Because the cart does not contain the optional medication, the caregiver is required to return to the central storage location 102 and retrieve it. This not only requires an additional trip by the caregiver, but wastes valuable time for the caregiver to attend to other medical needs of the patient.

Continuing, the next stop for the caregiver is room 106. The patient in room 106 does not request any optional medications and after administering the required medications to the patient, the caregiver proceeds to the next patient in room 108. This time, however, the patient in room 108 requests an optional medication for a sleeping aid or similar type of medication. Again, the caregiver would have to return to the central storage location 102 and retrieve the appropriate optional medication.

The caregiver then proceeds to rooms 110 and 112. At room 112, the caregiver for the third time returns to the central storage 102 and retrieves a user-requested optional medication. The caregiver then services the patients of rooms 114, 116, and 118. Each time the caregiver returns to the central storage location 102 for optional medications, the caregiver wastes valuable time that could have been used to take care of the patients.

Alternative implementations exist to servicing patients with optional medication requests. Accordingly, the caregiver could administer the required medications of the patients in rooms 104-118 first and then afterwards, administer optional medications that were requested while the caregiver was in the patient's room 104-118. The caregiver would still have to visit the central storage location 102 to retrieve the optional medications. The caregiver would also be required to write down or memorize each patient's optional medicinal needs. Still further, there may be considerable delay time when a first patient requests the optional medication and the response to that request by the caregiver.

In yet further embodiments, a request for optional medication can occur when the caregiver is in another patient's room 104-118. In response, the caregiver would retrieve the requested optional medications at the central storage location 102. The caregiver would then proceed to the requesting patient's room to dispense and administer the optional medication. The caregiver would then return to the room the caregiver was at before receiving the request.

In some embodiments, the optional medications may be stored on the medical cart. The optional medication, however, would have to be returned to the central storage location 102 when the caregiver has completed his/her routes. Consequently, the medication would be handled numerous times. For example, each time the medication is used, the medication would be loaded onto the cart and then unloaded at the central storage location 102 when the caregiver has completed his/her routes. Filling and restocking the medication would decrease the amount of time that the caregiver has for the other needs of the patients.

With reference now to FIG. 1b, a caregiver's route using multiple dispensing apparatuses for each individual's medicinal needs is presented. In addition to the apparatus used for dispensing required medications to each individual patient, another apparatus for dispensing optional medications within each individual patient's room 104-118 is used. Because each room 104-118 can individually dispense optional medications, each room 104-118 can be serviced without the caregiver returning to the central storage location 102. The caregiver can proceed to room 104, room 106, and so on without wasting valuable time. Thus, a caregiver can tend to the patient's other needs.

Figure 2:
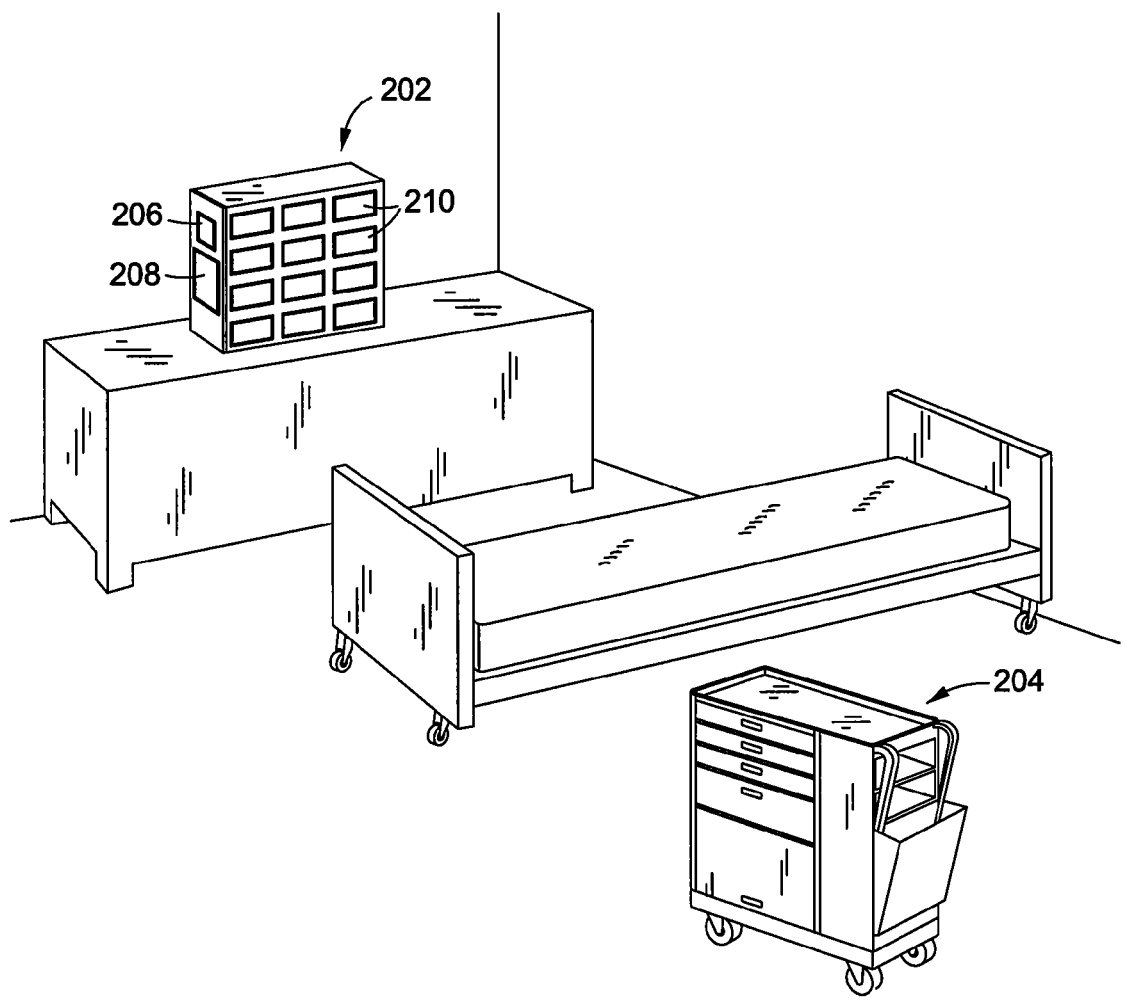
FIG. 2 is a block diagram of an individual patient's room along with a first and second apparatus for dispensing medications in accordance with embodiments of the present disclosure.

Now referencing FIG. 2, an apparatus for dispensing optional medications 202 located in, or in close proximity to, each room 104-118 in conjunction with a medical cart 204 movable to multiple rooms 104-118 is presented. Apparatus 202 can contain numerous compartments where each compartment can contain a different type of optional medication such as Tylenol, sleeping medications, etc. Combined with the medical cart 204, both required and optional medication administrations can be performed without leaving the room 104-118.

The dispensing apparatus 202 can contain a locking device 206 to limit access of the optional medications to the individual patients within the rooms 104-118. Such locking devices 206 would prevent drawers 210 of the dispensing apparatus 202 from being opened. One locking device 206 can be a lock and key device. Alternatively, the locking device 206 can be a fingerprint recognition device. Further, the locking device 206 can be a voice recognition system or a combination lock. One of ordinary skill in the art would recognize that there are many types of locking devices 206 that can prevent the apparatus 202 from being opened, or, in other words, there are many types of locking devices 206 that can restrict access to the optional medications in the dispensing apparatus 202 and that can provide access to the optional medications by only those authorized to retrieve the medications. In still yet other embodiments, the apparatus 202 does not need a locking device 206.

The dispensing apparatus 202 can also include a user interface 208 for the caregiver, or other authorized personnel, to provide instructions to the apparatus 202 relating to the requested optional medication. For instance, in some embodiments, the caregiver approaches the dispensing apparatus 202 and gains access to the user interface 208 by passing a security check provided by the locking device 206, which can be, for example, a fingerprint recognition device. Upon gaining access to the user interface 208 and having cleared the security check, the caregiver can specify which optional medication is requested. Upon receiving the request, the apparatus 202 can open one of the drawers and allow the caregiver to retrieve and administer the medication. In some embodiments, the user interface 208 is an LCD screen that displays the contents of the apparatus 202 and that provides input means, for example, a keyboard, buttons, or touch-screen, for the caregiver to provide input to the apparatus 202.

In further embodiments, the caregiver may specify the requested medication prior to passing the security check. This may be advantageous if various optional medications have differing degrees of security checks or if limitations are placed on particular medications due to potential conflicts with other required medications. To access the medication, the caregiver would approach the apparatus 202 and identify via the user interface 208 the requested medication. In some embodiments, the apparatus 202 confirms whether the medication is compatible with the medications currently being administered to the patient, and upon clearance, the apparatus 202 can request the caregiver to unlock or otherwise deactivate the locking device 206. Upon confirming that the caregiver is authorized to gain access to the optional medication, the apparatus 202 can then unlock the specific drawer 210 corresponding to the medication, open the drawer 210 containing the medication, or otherwise dispense the medication for the caregiver to administer.

In the embodiments shown in FIG. 2, the optional medicine dispensing apparatus 202 is affixed to the room. In some embodiments, the apparatus 202 can be affixed to the patient's bed. The apparatus 202 can also be affixed to a table near the patient. One of ordinary skill in the art would appreciate that the apparatus 202 can be attached to any item which is fixed. In some embodiments, the apparatus 202 may be movable within the patient's room 104-118. In yet other embodiments, the apparatus 202 is positioned in close proximity to the patient's room. For example, in some embodiments, the apparatus 202 is affixed to a wall outside the patient's room.

In some embodiments, the apparatus 202 can be actuable from a central location. For example, with reference to FIG. 4, the apparatus 202 can be configured to be operable by the caregiver at a terminal, or central control 212, located at the caregiver's station. When a patient desires to receive an optional medication, the patient can call the caregiver and make the request. Some embodiments provide that the caregiver is able to remotely open the apparatus 202 from the caregiver's station through the central control 212. This is particularly beneficial with ambulatory patients that are capable of getting out of bed and retrieving the medications without assistance. The central control 212 can be a terminal that is directly, wirelessly, or otherwise connected to one or more dispensing apparatus 202.

Figure 4:
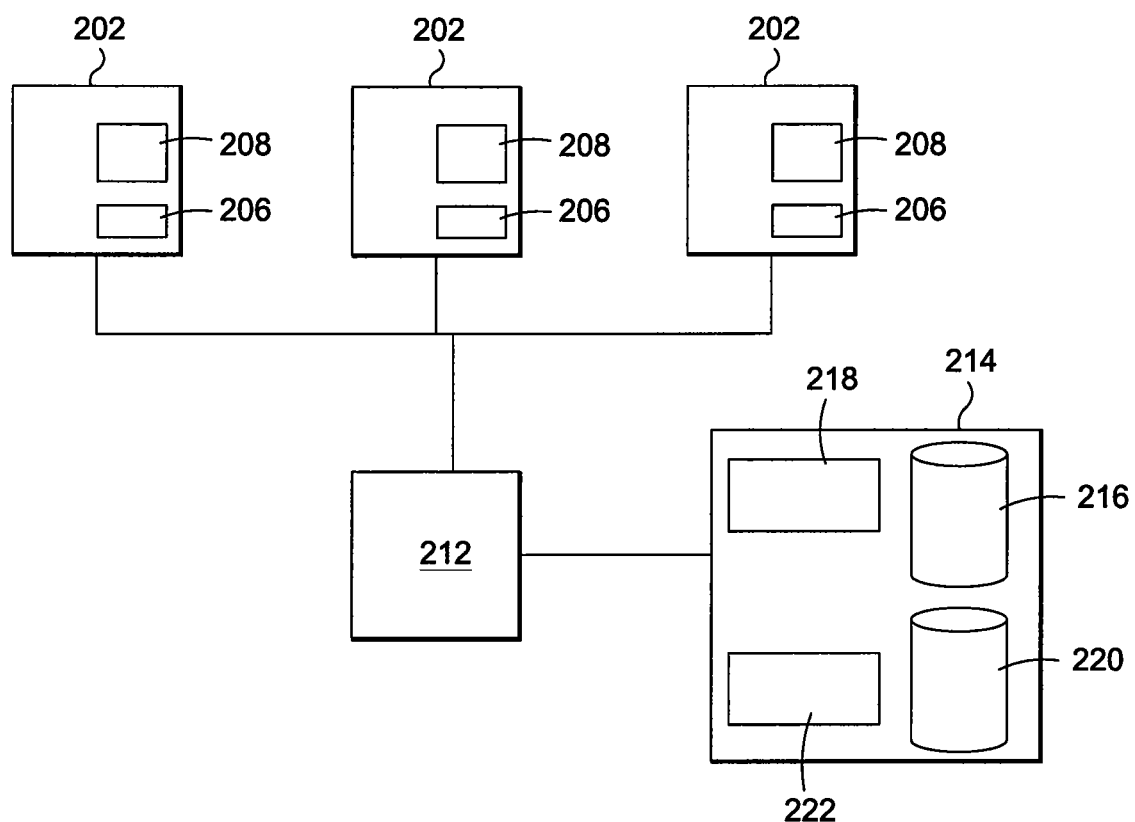
FIG. 4 depicts a schematic view of embodiments of a dispensing apparatus as discussed herein.

The central control 212 can also be similarly connected to other electronic modules at the care facility. For example, in some embodiments, as depicted in FIG. 4, the central control 212 is directly, wirelessly, or otherwise connected to a care facility management module 214. The care facility management module 214 can include an accounts receivable database 216 and accounts receivable processor 218 that keeps track of and processes all expenses for which a particular patient will be billed. In some embodiments, information from the administration of optional medication is automatically transmitted from the dispensing apparatus 202 to the accounts receivable database 216 through the central control 212 and accounts receivable processor 218. This information can be processed and automatically added to the patient's bill.

The care facility management module 214 can also include a personnel information database 220 and personnel information processor 222. The personnel information database 220 can include, among other things, information relating to accessing the dispensing apparatus 202 by care facility personnel. For example, the personnel database 220 can include a caregiver's fingerprint for verification when the caregiver attempts to obtain access to an apparatus 202 through a fingerprint reader. When the caregiver's fingerprint is read by the locking device 206 of the apparatus 202, the personnel information processor 222 or the central control 212 can access the personnel database to determine whether the caregiver is authorized to access the requested medication. Accordingly, a caregiver that is asked to care for patients in new rooms that the caregiver is not normally assigned is still able to gain access to the dispensing apparatus 202 in those new rooms because the caregiver's personnel information is stored at a centralized location that can be accessible to all dispensing apparatuses 202 in the care facility. Moreover, the administration of medications by a particular caregiver can also be monitored by retrieving from the personnel database the day and time that the caregiver sought access to any one or all dispensing apparatus 202 in the facility.

In some embodiments, records relating to how many medications remain within the apparatus 202 are preferably kept at the central control 212. Accordingly when any one medication needs to be replenished, a indicator may be provided on the apparatus or at the central control 212. In some embodiments, the indicator provides the name and quantity of optional medication that needs to be replaced.

Additionally, when the caregiver provides remote access to the apparatus 202, such as through the central control 212, the apparatus 202 preferably only provides access to a single dose of the requested optional medication. In some embodiments, the medications are contained within a drawer 210, and the drawer 210 is divided into compartments that are configured to only provide a single-dose of the medication. When the caregiver opens the drawer for the patient or a caregiver, whether remotely or otherwise, the drawer preferably only opens to the point that it provides the next dosage of medication. Accordingly, the apparatus 202 can monitor, or keep track of, what medications are stored within and dispensed from the apparatus 202.

Figure 3:
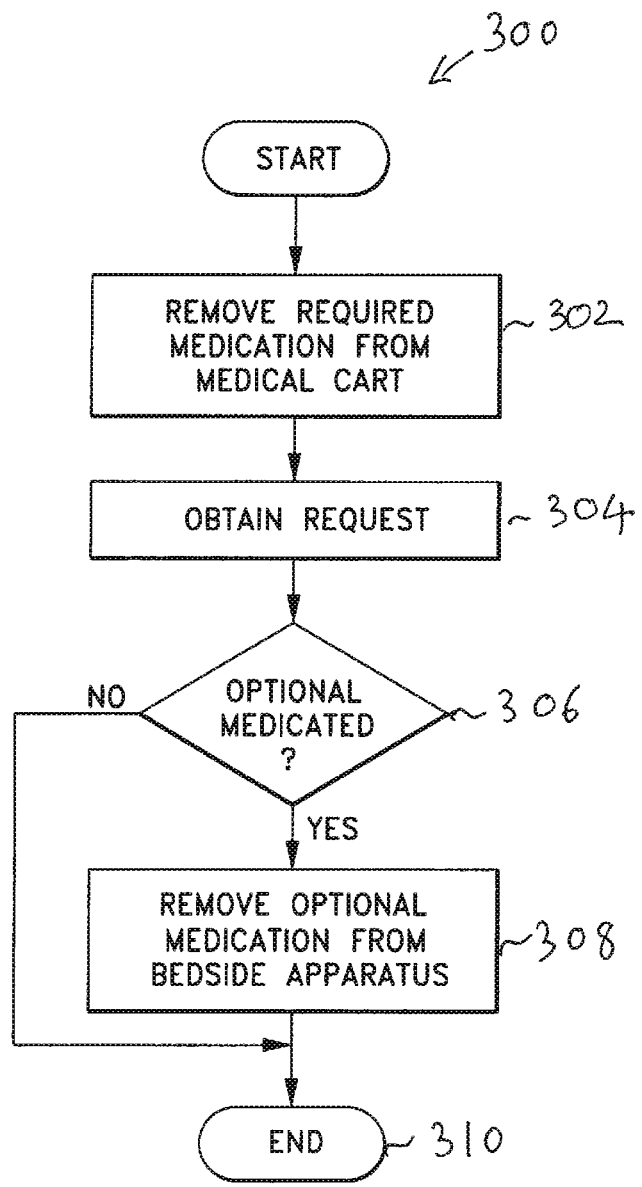
FIG. 3 is a flow diagram for dispensing medication corresponding to a patient's request in accordance with embodiments of the present disclosure.

Now referring to FIG. 3, a flow diagram 300 for using two dispensing apparatuses to timely satisfy a patient's request is presented. Beginning at block 302, the caregiver begins to administer the required medication from the medical cart 204 to the patient of the room 104-118. While the caregiver is in the room 104-118, the caregiver obtains a request made by the patient at block 304.

At determination block 306, the caregiver determines whether the request was for an optional medication. The caregiver removes the optional medication from the apparatus 202 and administers the optional medication to the patient at block 308 when there was a request for the optional medication. In some embodiments, the caregiver is required to unlock a device associated with the apparatus 202. The caregiver can use their key to open a lock. Alternatively, the caregiver can use their fingerprint signature to open the lock. Also, the caregiver can use their voice to open the lock. These are exemplary only, as other methods for authentication may be employed to control the unlocking of the device. Thereafter, the caregiver proceeds to the next room ending the patient's care at block 310.

In further embodiments of the present disclosure, the caregiver, who is located in another patient's room 104-118, receives a request from a patient in another room 104-118. To satisfy the request, the caregiver enters to the requesting patient's room 104-118 and removes the optional medicine from the dispensing apparatus 202 associated with the individual patient. By using the apparatus 202, valuable time is saved by not having to retrieve the optional medicine from the central storage station 102. Thereafter, the caregiver returns to the other patient's room 104-118.

In order to facilitate management of pharmaceutical needs, administrative information is logged each time the optional medication dispensing apparatus 202 is used. Either the caregiver can directly log the information or the apparatus 202 provides an automatic logging function. The apparatus 202 provides the information to an electronic inventory management device at the central storage location 102. In this way, the central storage location 102 can manage both the number of optional and required medications left and can make appropriate pharmaceutical requests.

In some embodiments, when the patient requests and receives optional medication, access to the apparatus 202 triggers an electronic signal that is processed by a processing unit to indicate with what medication the patient was treated. This can be used to keep records on medication intake as well as for billing purposes. For example, in some embodiments, when the patient requests optional medication, the apparatus 202 sends notification of the treatment to the patient's records for inclusion in billing the patient for the provided medications. Accordingly, the apparatus 202 provides automatic billing accountability for administering optional medications.

Through the use of the optional medication dispensing apparatus 202, fewer medications will be returned to the central storage location 102. Accordingly, the optional required medication can be left in the room 104-118 with the individual patients. By not refilling and restocking the optional medications, the medications are handled fewer times and increase the amount of time that a caregiver has to tend to other needs of the patients. Additionally, tighter controls are kept on the medication to reduce loss through, for example, staff use.

The optional medication dispensing apparatus 202 further permits the optional medication inventory to be adjusted by the caregiver, who is likely familiar with the needs of the individual patient and has access to bulk quantities of medications at the central storage location 102. As demand for certain medications changes, the caregivers can add or remove medications that are stored in the rooms. Moreover, by knowing what ailments the patient is suffering, or will likely suffer, the caregiver can provide specific medications in the dispensing apparatus 202 to ensure that such medications are not exhausted during the patient's time in the hospital or care facility. Additionally, if optional medications may have adverse effects when combined with the patient's required medication, the caregiver can selectively replace the optional medication in the dispensing apparatus 202 with medication that is more compatible with the required medication.

With the optional medication located in the dispensing apparatus 202, the caregiver is able to respond immediately to the patient's request and administer the medication. This quick response to the patient's request will increase patient satisfaction and can reduce stress and distress that may otherwise be experienced by a patient who has to wait long periods of time for a caregiver to retrieve optional medication. Additionally, the optional medication in the dispensing apparatus 202 reduces mistakes that may otherwise occur when the caregiver returns to the central storage location 102.

The description of the disclosure is provided to enable any person skilled in the art to practice the various embodiments described herein. While the present disclosure has been particularly described with reference to the various figures and embodiments, it should be understood that these are for illustration purposes only and should not be taken as limiting the scope of the disclosure.

There may be many other ways to implement the disclosure. Various methods and system described herein may be partitioned differently from those shown without departing from the spirit and scope of the disclosure. Various modifications to these embodiments will be readily apparent to those skilled in the art, and generic principles defined herein may be applied to other embodiments. Thus, many changes and modifications may be made to the disclosure, by one having ordinary skill in the art, without departing from the spirit and scope of the disclosure.

In the detailed description, numerous specific details were set forth to provide a full understanding of the present disclosure. It will be clear, however, to one ordinarily skilled in the art that the present disclosure may be practiced without some of these specific details. In other instances, well-known structures and techniques have not been shown in detail not to obscure the present disclosure.

What is claimed is:

1. A method for dispensing different types of medication to a plurality of patients, the method comprising:
    receiving, by an affixed secured first storage apparatus in a stationary location within an individual patient's room, a request for a medication from the individual patient;
    determining, by a medication dispensing system, if the requested medication is an optional medication;
    confirming, via the first storage apparatus, compatibility of the requested medication with medications currently being administered to the individual patient;
    selectively dispensing the requested medication, only if the requested medication is an optional medication compatible with medications currently being administered to the individual patient, from the affixed secured first storage apparatus; and
    dispensing, from a separate mobile second storage apparatus carrying required medications for the plurality of patients, one of the required medications for the individual patient, the second storage apparatus being movable between patient rooms with the affixed secured first storage apparatus remaining in the stationary location within the individual patient's room.

2. The method of claim 1, further comprising repeating the method for each individual patient within the plurality of patients.

3. The method of claim 1, wherein dispensing the optional medication from the affixed secured first storage apparatus comprises unlocking a security mechanism on the affixed secured first storage apparatus.

4. The method of claim 1, further comprising:
    automatically logging administrative information corresponding to dispensing from the affixed secured first storage apparatus; and
    managing the administrative information from a central control.

5. The method of claim 1, wherein the optional medications comprise non-prescription medications.

6. The method of claim 1, further comprising associating medication dispensed from the affixed secured first storage apparatus with the individual patient for billing purposes.

7. The method of claim 6, further comprising automatically billing the individual patient for optional medications dispensed for the individual patient from the affixed secured first storage apparatus.

8. The method of claim 1, further comprising responding at the affixed secured first storage apparatus to instructions provided from a central control to dispense the optional medications.

9. The method of claim 1, further comprising limiting access to only one dose of the optional medications in response to the request for the optional medications.

10. The method of claim 1, wherein dispensing the requested medication comprises remotely providing instructions to the affixed secured first storage apparatus to provide the individual patient with access to the optional medication.

11. The method of claim 1, further comprising replenishing the optional medications within the affixed secured first storage apparatus based on projected needs of the individual patient.

12. The method of claim 1, wherein the affixed secured first storage apparatus is accessed by at least one of a lock and key set, fingerprint recognition device, and voice recognition device.

13. A method for dispensing different types of medication to a plurality of patients, the method comprising:
   determining, by a medication dispensing system, if a medication requested from an individual patient is an optional medication;
   confirming, via an affixed secured first storage apparatus stationarily located within the individual patient's room, compatibility of the requested medication with medications currently being administered to the individual patient;
   selectively dispensing the requested medication, after confirming the requested medication is an optional medication compatible with medications being administered to the individual patient from the affixed secured first storage apparatus; and
   dispensing, from a separate mobile second storage apparatus carrying required medications for the plurality of patients, one of the required medications for the individual patient, the second storage apparatus being movable between patient rooms with the affixed secured first storage apparatus remaining stationarily located within the individual patient's room,
   wherein the optional medications comprise non-prescription medications and the required medications comprise prescription medications.

14. The method of claim 13, further comprising repeating the method for each individual patient of the plurality of patients.

15. The method of claim 13, wherein selectively dispensing the optional medication from the affixed secured first storage apparatus comprises unlocking a security mechanism on the affixed secured first storage apparatus.

16. The method of claim 13, further comprising:
   automatically logging administrative information corresponding to dispensing from the affixed secured first storage apparatus; and
   managing administrative information from a central control.

17. The method of claim 13, further comprising associating medication dispensed from the affixed secured first storage apparatus with a billing record of the individual patient.

18. The method of claim 13, further comprising responding at the affixed secured first storage apparatus to instructions provided from a central control to dispense the optional medications.

19. The method of claim 13, wherein dispensing the first medication comprises remotely providing instructions to the affixed secured first storage apparatus to provide the individual patient with access to the optional medication.

* * * * *

UNITED STATES PATENT AND TRADEMARK OFFICE
CERTIFICATE OF CORRECTION

PATENT NO. : 10,037,646 B2  
APPLICATION NO. : 11/928928  
DATED : July 31, 2018  
INVENTOR(S) : Heffron Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 156 days.

Signed and Sealed this
Thirtieth Day of July, 2019

Andrei Iancu
*Director of the United States Patent and Trademark Office*